United States Patent [19]

Ross

[11] Patent Number: 4,905,882
[45] Date of Patent: Mar. 6, 1990

[54] NECK ENGAGING SUPPORT FOR MEDICAL DEVICE

[76] Inventor: Judy L. Ross, 6737 Old Waterloo Rd. #113, Baltimore, Md. 21227

[21] Appl. No.: 291,171

[22] Filed: Dec. 28, 1988

[51] Int. Cl.$^4$ .............................................. A45F 5/00
[52] U.S. Cl. ........................... 224/265; 128/DIG. 6; 224/148; 224/181; 224/201
[58] Field of Search ............... 224/181, 186, 188, 189, 224/201, 222, 254, 255, 265, 266, 268, 148; 128/DIG. 6, DIG. 26; 604/179, 182; 248/95

[56] References Cited

U.S. PATENT DOCUMENTS

| | | | |
|---|---|---|---|
| 279,706 | 6/1883 | Carroll | 224/268 X |
| 893,998 | 7/1908 | Harris | 224/265 |
| 910,238 | 1/1909 | Shaw . | |
| 1,178,628 | 4/1916 | Clawson . | |
| 1,660,740 | 2/1928 | Bailey . | |
| 2,071,243 | 2/1937 | Tripp | 224/265 |
| 2,289,945 | 7/1942 | Wadsack . | |
| 2,494,632 | 1/1950 | Rodin | 224/148 |
| 2,510,646 | 6/1950 | Meers | 224/265 |
| 2,550,554 | 4/1951 | Griffin | 224/201 X |
| 2,602,575 | 7/1952 | Olson | 224/201 |
| 2,652,050 | 9/1953 | Schoeller | 224/268 |
| 2,723,665 | 11/1955 | Goldsmith | 128/DIG. 6 |
| 2,733,845 | 2/1956 | Biro | 224/201 |
| 3,197,099 | 7/1965 | Doba | 224/201 X |
| 3,225,982 | 12/1965 | Melton | 224/202 |
| 3,547,322 | 12/1970 | Dawson et al. | 224/265 |
| 4,438,763 | 3/1984 | Zablen | 224/265 X |
| 4,684,367 | 8/1987 | Schaffer . | |

Primary Examiner—Ernest G. Cusick
Attorney, Agent, or Firm—Fleit, Jacobson, Cohn, Price, Holman & Stern

[57] ABSTRACT

A neck engaging support for a medical device or appliance that engages and is thus supported from the neck of a medical practitioner. More specifically, the present invention is a rod-like support device having a downwardly opening, generally U-shaped hook member dimensioned to fit around the neck of a user with the open area positioned in front of the chest region with one leg of the U-shaped member having a smaller hook for engagement with an IV bag in order to support the IV bag in elevated position without using the hands such as is frequently necessary during emergency situations when a patient is being conveyed on a stretcher from the site of the emergency to an ambulance, hospital or the like. The support of this invention enables the user of the device to actually carry one end of the stretcher while at the same time supporting an IV bag in an elevated position. The rod-like support is constructed of thermoplastic material which can be obtained in straight condition and heated to a temperature that enables it to be deformed to fit individual users with the thermoplastic rod then becoming set in the desired shape when the rod cools thereby enabling the device to be custom fitted to individual users although they can be constructed of standard sizes since the plastic rod will have some degree of flexibility to enable it to be quickly and easily positioned around the neck of the user.

3 Claims, 1 Drawing Sheet

NECK ENGAGING SUPPORT FOR MEDICAL DEVICE

BACKGROUND OF THE INVENTION

1. Field of the Invention

The present invention generally relates to a neck engaging support for a medical device or appliance that engages and is thus supported from the neck of a medical practitioner. More specifically, the present invention is a rod-like support device having a downwardly opening, generally U-shaped hook member dimensioned to fit around the neck of a user with the open area positioned in front of the chest region with one leg of the U-shaped member having a smaller hook for engagement with an IV bag in order to support the IV bag in elevated position without the hands such as is frequently necessary during emergency situations when a patient is being conveyed on a stretcher from the site of the emergency to an ambulance, hospital or the like. The support of this invention enables the user of the device to actually carry one end of the stretcher while at the same time supporting an IV bag in an elevated position. The rod-like support is constructed of thermoplastic material which can be obtained in straight condition and heated to a temperature that enables it to be deformed to fit individual users with the thermoplastic rod then becoming set in the desired shape when the rod cools thereby enabling the device to be custom fitted to individual users although they can be constructed of standard sizes since the plastic rod will have some degree of flexibility to enable it to be quickly and easily positioned around the neck of the user.

2. Information Disclosure Statement

Hook-like structures forming a support for various implements are well-known including flexible necklaces, chains and the like having a hook connected thereto for supporting musical instruments. The following U.S. patents are relevant to the concept of providing hook-like supports.

279,706
910,238
1,178,628
1,474,728
1,660,740
2,289,945
2,494,632
2,550,554
2,652,050
2,733,845
2,905,539
3,197,099
3,225,982
3,547,322
4,684,367

None of the above-mentioned patents discloses a rod-like structure constructed in the manner of the present invention for effectively supporting an IV bag in elevated position in relation to a patient when the patient is being transported or otherwise undergoing emergency care thereby enabling the user of the invention to utilize their hands for performing various necessary functions relating to patient care.

SUMMARY OF THE INVENTION

An object of the present invention is to provide a neck engaging support for a medical device, appliance or apparatus which includes a rod-like structure having a large U-shaped or hook-shaped member engaging the neck with a smaller hook at one end thereof for supportingly engaging a medical device or appliance such as the aperture normally provided in the upper end of a flexible IV bag to support the IV bag in elevated position when transporting a patient on a stretcher in conditions where a conventional IV bag support post or rod is not available.

Another object of the invention is to provide a neck engaging support in accordance with the preceding object which enables a person to "hold" an IV bag during emergency care with the support being quickly and easily placed around the neck and being free to easily move with the person using the device. The support is especially useful by ambulance personnel carrying a stretcher, medical personnel performing CPR and by other medical personnel that find it necessary to have free use of their hands for purposes other than holding an IV bag thereby reducing the need of having additional personnel available either to hold the IV bag or perform some other function.

A further object of the invention is to provide a neck engaging support for an IV bag constructed of an extruded plastic rod that can be heated and shaped to the contour of the average neck and upper chest area with the support being provided with rounded ends to prevent injury to the user and to prevent the device from being entangled with the clothing of the user.

A still further object of the invention is to provide a support of one-piece construction having a relatively large U-shaped member or hook-shaped member forming the major portion of the support with the end of one leg of the support having a small reversely bent hook of U-shaped configuration to engage an aperture normally provided in the end flap or flange on an IV bag with the support being easily placed in operative position, easily removed, lightweight, sturdy, easy to maintain in a clean condition and effective to enable medical personnel to support an IV bag in optimum elevated position while leaving the hands free to perform other functions rather than using one hand to hold the IV bag in an elevated position.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
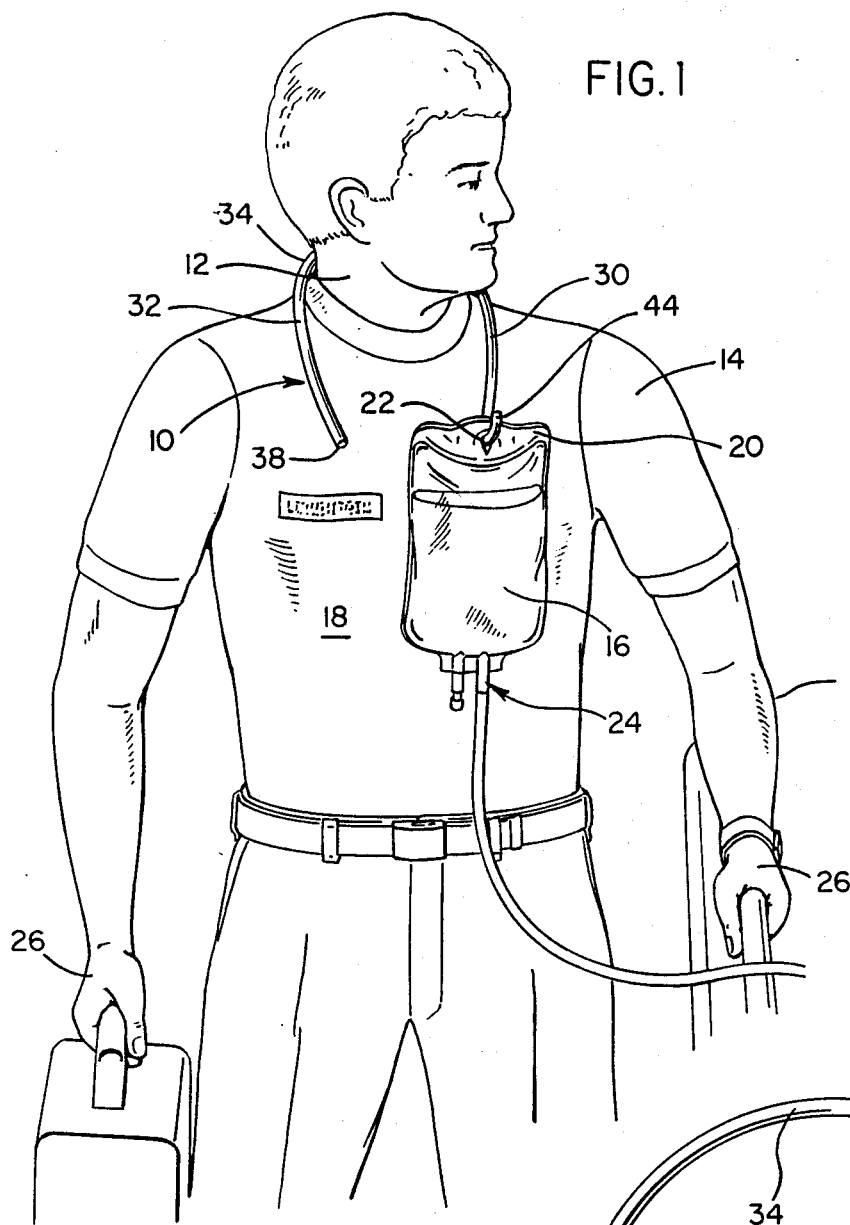
FIG. 1 is a perspective view of the neck engaging support of the present invention illustrating the manner in which it can be used.
Figure 2:
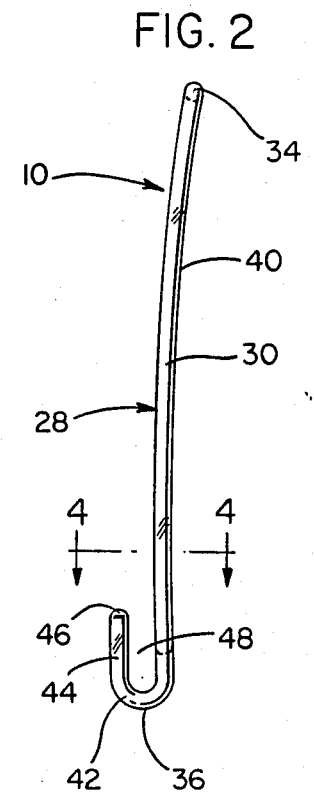
FIG. 2 is a side elevational view of the support.
Figure 3:
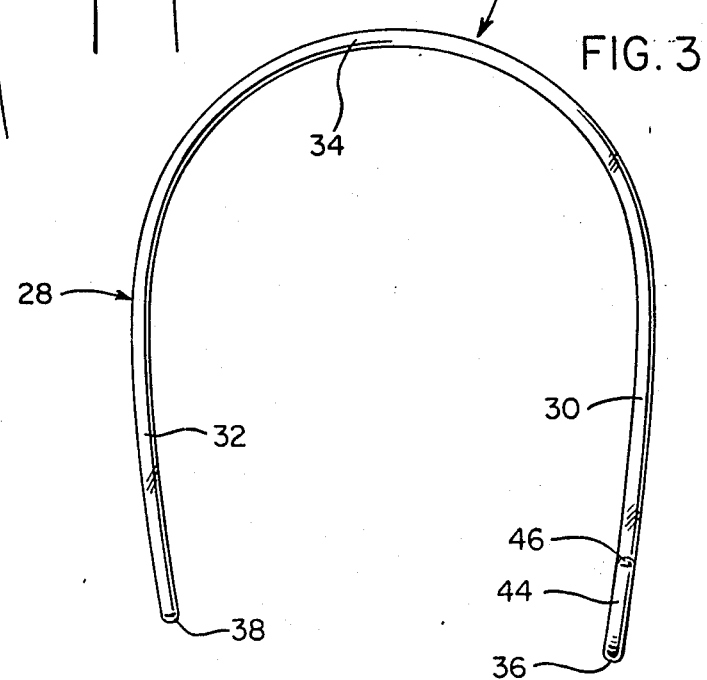
FIG. 3 is a front elevational view of the support.
Figure 4:
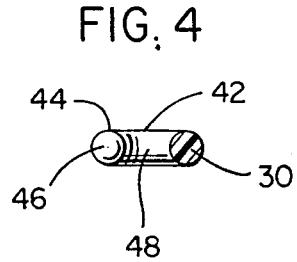
FIG. 4 is a sectional view taken along section line 44 on FIG. 2 illustrating the relationship of the small hook to the remainder of the support.

Referring now specifically to the drawings, the neck engaging support of the present invention is generally designated by reference numeral 10. As illustrated in FIG. 1, the support 10 is positioned around the neck 12 of an individual user 14 such as an ambulance driver, paramedic, person engaged in administering CPR or other medical personnel for supporting an IV bag 16 in elevated position against the front surface of the chest area 18 of the user. The IV bag 16 is conventional and includes the usual flange or flap 20 having an aperture 22 therein which normally engages a hook support at the upper end of an IV pole or post. The IV bag includes the usual fittings, tubes, control devices and the like 24 with the support 10 of the present invention providing an effective support for the IV bag to enable the user 14 to have the hands 26 free for performing functions other than holding the IV bag 16 in elevated position. This is especially useful when an ambulance driver or other medical personnel is carrying a stretcher, administering CPR and the like inasmuch as this enables a single person to not only "hold" the IV bag but also perform other functions in an effective manner thereby reducing the need for an additional person to hold the IV bag during emergency care situations.

The support 10 includes an elongated plastic rod 28 of circular cross-sectional configuration throughout its length with the rod being of the same diameter throughout its length and being lightweight and substantially rigid but with sufficient flexibility to enable the support to be easily and quickly placed around the neck or removed therefrom. The support includes an enlarged U-shaped component or hook component defined by legs 30 and 32 connected together by a web or bight portion 34 with the legs 30 and 32 converging slightly towards their free ends 36 and 38 and also curving slightly with a concave inner surface 40 generally conforming with the surface area of the chest 18 of the user 14. The free end 36 of the leg 30 is formed as a U-shaped hook member 42 which includes a short upwardly extending leg 44 generally parallel to and spaced from the leg 30 and terminating in a rounded end 46 thus defining an upwardly opening access area 48 to form a supporting hook which has the rounded end 46 inserted through the opening 22 in the IV bag 16 to effectively support the IV bag 16 in a secure manner but yet enable removal of and replacement of the IV bag when desired. The plastic rod 28 is of one piece continuous construction and is preferably constructed of a plastic material having thermoplastic characteristics which, when heated, will enable a straight rod to be deformed or molded into the desired shape with the shaped plastic rod then becoming set when the rod cools. The plastic rod may be clear, transparent, translucent or any desired color and the smooth external surface thereof will be easy to clean and will eliminate possible injury to the user and avoid damage to clothing and prevent entanglement with clothing or other medical devices, apparatuses and the like.

Various medical personnel can use the neck engaging support to "hold" an IV bag in optimum elevated condition in an effective and convenient manner while leaving their hands free to perform other functions especially during emergency care such as an ambulance driver carrying a stretcher, medical personnel administering CPR or other emergency procedures. By freeing the hands of the user, the number of medical personnel required during an emergency care situation can be reduced. The neck engaging support can be easily placed around the neck and will move easily with the person using the device and has sufficient strength and rigidity to effectively support a conventional IV bag. The lightweight and smooth external characteristics enable the device to be worn without hindrance to normal functions of the user. The distance between the terminal ends 36 and 38 may approximate the diameter of the neck of an average person and the resilient flexible characteristics of the plastic will enable the ends to be flexed apart if necessary when placing it around the neck. The general parallel arrangement of the legs 30 and 32 and their inward curving convergence will assure that the support will stay in position loosely around the neck with the ends 36 and 38 resting against the chest 18 with the IV bag 16 also resting against the chest surface unless leaning forwardly in which event the hook-shaped configuration of the small supporting hook will retain the IV bag in place.

While the drawings depict the support used by medical personnel, the open ended, U-like shape of the support adapts it for home use even by bedridden patients. An extension may be formed on the end of leg 30 which extends upwardly from the surface of the chest with the hook 42 at the upper end of the extension supporting the IV bag above the bedridden patient.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. In combination, an IV bag having a flange at its upper end, said flange including a centrally disposed aperture to support the IV bag from a support, a neck engaging support including a small hook opening upwardly to supportingly engage the IV bag by insertion of the small hook through said aperture, an enlarged open ended, generally U-shaped neck engaging member integral with the small hook with the neck engaging member including spaced legs of elongated configuration interconnected by a curved web with free ends of the legs being spaced apart sufficiently to be positionable laterally onto the neck of a user to provide support for the IV bag from the neck engaging support for leaving the hands of the user free to perform other functions.

2. The combination as defined in claim 1 wherein said support is of one-piece plastic rod construction having rounded ends and smooth external surfaces to prevent injury and entanglement with clothing and permit easy cleaning.

3. The combination as defined in claim 1 wherein said U-shaped member is curved so as to conform with the front surface of the chest region of a user, said small hook laterally from the lower end of one leg of the U-shaped member so as to project forwardly from the front surface of the chest region of a user.

* * * * *